US008829019B2

(12) United States Patent
Ohta et al.

(10) Patent No.: US 8,829,019 B2
(45) Date of Patent: Sep. 9, 2014

(54) STABLE TABLET CONTAINING 4,5-EPOXYMORPHINAN DERIVATIVE

(75) Inventors: Kotoe Ohta, Kamakura (JP); Suguru Takaki, Kamakura (JP); Yasuhide Horiuchi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 13/125,726

(22) PCT Filed: Oct. 23, 2009

(86) PCT No.: PCT/JP2009/068228
§ 371 (c)(1),
(2), (4) Date: Apr. 22, 2011

(87) PCT Pub. No.: WO2010/047381
PCT Pub. Date: Apr. 29, 2010

(65) Prior Publication Data
US 2012/0114752 A1 May 10, 2012

(30) Foreign Application Priority Data

Oct. 24, 2008 (JP) ................................. 2008-274579

(51) Int. Cl.
*A61K 31/44* (2006.01)
*A61K 9/00* (2006.01)
*A61K 9/16* (2006.01)
*A61K 9/20* (2006.01)
*A61K 31/485* (2006.01)

(52) U.S. Cl.
CPC ............. *A61K 9/2059* (2013.01); *A61K 9/2009* (2013.01); *A61K 9/2018* (2013.01); *A61K 31/485* (2013.01); *A61K 9/1623* (2013.01); *A61K 9/1676* (2013.01); *A61K 9/2027* (2013.01)
USPC ........... 514/282; 424/494; 424/490; 424/400; 424/464

(58) Field of Classification Search
None
See application file for complete search history.

(56) References Cited

U.S. PATENT DOCUMENTS

| 6,372,755 | B2 * | 4/2002 | Hanamura et al. ............ 514/282 |
| 6,572,891 | B1 | 6/2003 | Ugarkovic |
| 2,597,475 | A1 * | 10/2009 | Kawasaki et al. ............ 514/183 |
| 2001/0004637 | A1 | 6/2001 | Hanamura et al. |
| 2005/0008698 | A1 * | 1/2005 | Maruyama .................... 424/465 |
| 2007/0196494 | A1 | 8/2007 | Grenier et al. |
| 2007/0224129 | A1 * | 9/2007 | Guimberteau et al. ...... 424/10.2 |
| 2013/0156859 | A1 * | 6/2013 | Koshi et al. ................... 424/493 |

FOREIGN PATENT DOCUMENTS

| EP | 0948965 A1 * | 11/1997 |
| EP | 0 948 965 A1 | 10/1999 |
| JP | 2005-2123 A | 1/2005 |
| WO | WO 2008/015220 A1 | 2/2008 |
| WO | WO 2008015220 A1 * | 2/2008 |

OTHER PUBLICATIONS

Buhler, Insoluble polyvinylpyrrolidone (Crospovidone), in Polyvinylpyrrolidone Excipients for Pharmaceuticals, 2005, 125-178.*
Edited by Japan Pharmaceutical Excipients Council, Iyakuhin Tenkabutsu Jiten, 1st edition, Yakuji Nippo Ltd., 1994, pp. 31, 46.
International Search Report, dated Jan. 12, 2010 issued in PCT/JP2009/068228.
European Office Action dated Apr. 8, 2013 for Application No. 09 82 2078.
S Edge, "Sodium Starch Glycolate", Handbook of Pharmaceutical Excipients, Pharmaceutical Press, London, 2006, pp. 701-704, XP-002694443.
Translation of Chinese Office Action for Application No. 200980142056.8.

* cited by examiner

*Primary Examiner* — Svetlana M Ivanova
(74) *Attorney, Agent, or Firm* — Birch, Stewart, Kolasch & Birch, LLP

(57) ABSTRACT

The present invention relates to a stable tablet comprising a 4,5-epoxymorphinan derivative or a pharmacologically acceptable acid addition salt thereof as an effective ingredient. That is, the tablet according to the present invention comprises: (1) as the effective ingredient, a specific 4,5-epoxymorphinan derivative or a pharmacologically acceptable acid addition salt; (2) sodium thiosulfate; (3) at least one selected from the group consisting of saccharides and sugar alcohols; and (4) crospovidone, sodium carboxymethyl starch or a mixture thereof, in which tablet the content of the aforementioned (4) is 1 to 20% by weight per unit weight containing the aforementioned effective ingredient.

12 Claims, No Drawings

STABLE TABLET CONTAINING 4,5-EPOXYMORPHINAN DERIVATIVE

TECHNICAL FIELD

The present invention relates to a stable tablet of a 4,5-epoxymorphinan derivative or a pharmacologically acceptable acid addition salt thereof.

BACKGROUND ART

A 4,5-epoxymorphinan derivative represented by the Formula (I) (described later) or a pharmacologically acceptable acid addition salt thereof, which is the effective ingredient of the present invention, has prominent antipruritic effect and has been disclosed as a compound effective as a therapeutic drug for pruritus in a variety of diseases accompanying pruritus (for example, see Patent Document 1). However, the aforementioned 4,5-epoxymorphinan derivative has been known to be chemically unstable to light, heat and oxygen, and with regard to the method of stabilizing such 4,5-epoxymorphinan derivative, it is described that a stable pharmaceutical composition can be obtained by allowing the composition to contain a saccharide(s) or sugar alcohol(s) and an antioxidant such as sodium thiosulfate (see Patent Document 2). Yet, when the present inventors examined tableting of the 4,5-epoxymorphinan derivative represented by the Formula (I) or a pharmacologically acceptable acid addition salt thereof, it was revealed that, although a conventionally known stabilization method in which an antioxidant such as sodium thiosulfate is added is effective for stabilization of the effective ingredient in a liquid-form, in cases where the method is employed for a tablet, it is difficult to obtain a tablet whose decomposition is minimized over a long period of time in unpacked state or in a normal package form and which maintains sufficient stability as a tablet.

Conventionally, as a method of stabilizing various morphinan compounds including morphine, a technique of adding a basic component to morphine (for example, see Patent Document 3) and a method in which an antioxidant such as sodium thiosulfate or tocopherol is combined with naloxone (for example, see Patent Document 4), as well as a method in which a chelating agent and a citrate buffer are added to methylnaltrexone (for example, see Patent Document 5) and a method in which an organic acid and a chelate forming agent are blended with naltrexone hydrochloride (for example, see Patent Document 6), have been disclosed. However, none of these reports includes any description with regard to the type and the content of disintegrating agent effective in stabilization, and the stabilization effect imparted to a tablet by a specific disintegrating agent, crospovidone or sodium carboxymethyl starch, has not been revealed.

Meanwhile, as a tablet which comprises a saccharide such as lactose or a sugar alcohol such as mannitol or erythritol and, as disintegrating agent, crospovidone or sodium carboxymethyl starch, an intraorally disintegrating-type tablet which is intended for improving the dose compliance and can be taken without water has been disclosed (for example, see Patent Document 7). However, all of such reports merely disclose a tablet which has superior intraoral quick disintegration property along with formulation strength at a level which does not pose a problem in handling, and the stabilization effect imparted by crospovidone or sodium carboxymethyl starch has not been reported.

In addition, as a method of stabilizing a drug by blending crospovidone or sodium carboxymethyl starch, there are reports that fast release property is attained and drug hydrolysis is suppressed by blending crospovidone with sarpogrelate hydrochloride (see Patent Document 8); that a preparation which has both disintegration property and tablet hardness, as well as excellent storage stability over a long period of time, is attained by blending crospovidone or sodium carboxymethyl starch with iguratimod (see Patent Document 9); and that the stability is improved by blending crospovidone with vitamin or the like (for example, see Patent Document 10 and Non-patent Document 1). However, needless to say, since the mechanism of drug destabilization is largely dependent on the chemical structure and physiochemical properties of the drug, these reports offer no suggestion with regard to the stability of the effective ingredient of the present invention, which is a 4,5-epoxymorphinan derivative represented by the Formula (I) or a pharmacologically acceptable acid addition salt thereof.

PRIOR ART DOCUMENTS

Patent Documents

Patent Document 1: JP 3531170 B
Patent Document 2: WO 99/02158
Patent Document 3: JP 2-160719 A
Patent Document 4: WO 98/35679
Patent Document 5: WO 2004/091623
Patent Document 6: Japanese Translated PCT Patent Application Laid-open No. 2005-531515
Patent Document 7: WO 97/47287
Patent Document 8: JP 2007-56011 A
Patent Document 9: JP 2007-224021 A
Patent Document 10: JP 2002-302446 A Non-Patent Document Non-patent Document 1: Volker Buehler, "Kolldon Polyvnylpyrrolidon for the pharmaceutical industry", BASF brochure, pp. 186-187, August 1993 (2nd edition, published in August 1993)

SUMMARY OF THE INVENTION

Problems to be Solved by the Invention

An object of the present invention is to provide a stable tablet comprising a 4,5-epoxymorphinan derivative or a pharmacologically acceptable acid addition salt thereof as an effective ingredient.

Means for Solving the Problems

In order to develop a stable tablet capable of enduring in unpacked state and long-term storage, the present inventors intensively studied to discover that, among those disintegrating agents commonly used for formulation, only crospovidone and sodium carboxymethyl starch can, when made to co-exist with sodium thiosulfate and a saccharide or sugar alcohol, allow a 4,5-epoxymorphinan derivative or a pharmacologically acceptable acid addition salt thereof to more stably exist in a tablet, thereby completing the present invention.

That is, the present invention relates to the following inventions.
[1] A tablet comprising the following (1) to (4):
(1) as an effective ingredient, a 4,5-epoxymorphinan derivative represented by the Formula (I) (described later) or a pharmacologically acceptable acid addition salt thereof;
(2) sodium thiosulfate;

(3) at least one selected from the group consisting of saccharides and sugar alcohols; and
(4) crospovidone, sodium carboxymethyl starch or a mixture thereof, in which tablet the content of the aforementioned (4) is 1 to 20% by weight per unit weight containing the aforementioned effective ingredient.
[2] The tablet according to [1], wherein the aforementioned (3) is at least one selected from the group consisting of potato starch, saccharose, lactose, mannitol, erythritol and maltitol.
[3] The tablet according to [1] or [2], wherein a part or the entirety of the aforementioned (3) is granulated granules.
[4] The tablet according to [3], wherein the aforementioned granulated granules are produced by extrusion granulation, stirring granulation, spray drying or fluidized bed granulation.
[5] The tablet according to any one of [1] to [4], the tablet being produced by a production method comprising the steps of dissolving or suspending the aforementioned effective ingredient in water or a pharmacologically acceptable solvent and adding the resulting liquid to the aforementioned saccharide or sugar alcohol.
[6] The tablet according to any one of [1] to [5], wherein the tablet is in a coated form.

Effects of the Invention

By allowing a tablet to comprise, as the effective ingredient, a 4,5-epoxymorphinan derivative represented by the Formula (I) (described later) of the present invention or a pharmacologically acceptable acid addition salt thereof and blending thereto crospovidone or sodium carboxymethyl starch in a prescribed amount, a fast-disintegrating tablet or an intraorally disintegrating tablet which has superior storage stability and remains highly stable even after a long time since its production can also be produced.

MODE FOR CARRYING OUT THE INVENTION

The tablet according to the present invention will now be described. The indispensable components of the tablet according to the present invention are:
(1) a 4,5-epoxymorphinan derivative represented by the Formula (I) (described later) or a pharmacologically acceptable acid addition salt thereof (effective ingredient);
(2) sodium thiosulfate;
(3) at least one selected from the group consisting of saccharides and sugar alcohols; and
(4) crospovidone, sodium carboxymethyl starch or a mixture thereof.
The component (4) is contained in an amount of 1 to 20% by weight per unit weight containing the effective ingredient. The phrase "unit containing the effective ingredient" used herein refers to a solid component unit directly in contact with the effective ingredient in the preparation, and in the case of a film-coated tablet, it refers to the core of the tablet, which is an essential part affecting the drug stability. The phrase "% by weight per unit weight containing the effective ingredient" used herein means a weight percentage with respect to the weight of the solid component unit directly in contact with the effective ingredient in the preparation. A tablet comprising the components (2) to (4) has a reduced decomposition of the effective ingredient (1) and stably comprises the effective ingredient even after a long period of time. The stability of the effective ingredient in a tablet can be evaluated by, for example, leaving the tablet to stand in an open state under the condition of 40° C./75% RH, which is the acceleration condition described in the Drug Approval and Licensing Procedures in Japan (2006), and subsequently measuring the residual ratio of the effective ingredient in the tablet by HPLC method or the like.

The indispensable component (1) of the tablet according to the present invention is a 4,5-epoxymorphinan derivative represented by the following Formula (I) or a pharmacologically acceptable acid addition salt thereof

[Formula 1]

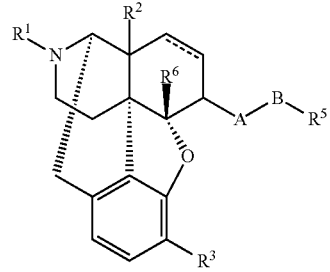

(I)

Here, in the Formula (I), the double line composed of a dashed line and a solid line represents a double bond or a single bond; R' represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, $C_1$-$C_5$ furan-2-ylalkyl or $C_1$-$C_5$ thiophen-2-ylalkyl; $R^2$ represents hydrogen, hydroxy, nitro, $C_1$-$C_5$ alkanoyloxy, $C_1$-$C_5$ alkoxy, $C_1$-$C_5$ alkyl or —$NR^7R^8$; $R^7$ represents hydrogen or $C_1$-$C_5$ alkyl; $R^8$ represents hydrogen, $C_1$-$C_5$ alkyl or —C(=O)$R^9$; $R^9$ represents hydrogen, phenyl or $C_1$-$C_5$ alkyl; $R^3$ represents hydrogen, hydroxy, $C_1$-$C_5$ alkanoyloxy or $C_1$-$C_5$ alkoxy; A represents —$N(R^4)$C(=X)—, —$N(R^4)$C(=X)Y—, —$N(R^4)$— or —$N(R^4)$SO$_2$— (wherein X and Y independently represent $NR^4$, S or O; $R^4$ represents hydrogen, $C_1$-$C_5$ linear or branched alkyl or $C_6$-$C_{12}$ aryl; and $R^4$ in the formula may be the same or different); B represents a valence bond or $C_1$-$C_{14}$ linear or branched alkylene (with the provisos that the alkylene is optionally substituted by at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl, trifluoromethoxy and phenoxy, and that 1 to 3 methylene groups may be substituted by carbonyl group(s)), $C_2$-$C_{14}$ linear or branched acyclic unsaturated hydrocarbon containing 1 to 3 double bonds and/or triple bonds (with the provisos that the acyclic unsaturated hydrocarbon is optionally substituted by at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl, trifluoromethoxy and phenoxy, and that 1 to 3 methylene groups may be substituted by carbonyl group(s)) or $C_1$-$C_{14}$ linear or branched saturated or unsaturated hydrocarbon containing 1 to 5 thioether bonds, ether bonds and/or amino bonds (with the provisos that a hetero atom does not directly binds to A, and that 1 to 3 methylene groups may be substituted by carbonyl group(s)); and $R^5$ represents hydrogen or an organic group having a basic skeleton shown below (with the proviso that the organic group is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy).

[Formula 2]

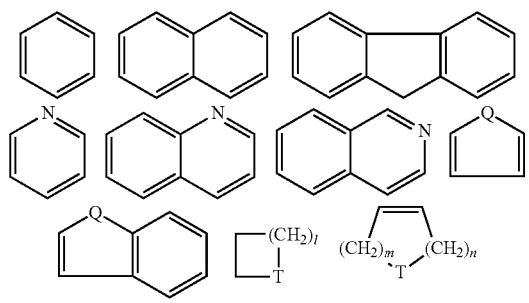

Q: N, O, S
T: CH, N, S, O
l = 0-5
m, n ≥ 0
m + n ≤ 5

Organic groups represented by $R^5$ $R^6$ represents hydrogen, $C_1$-$C_5$ alkyl or $C_1$-$C_5$ alkanoyl.

The double line composed of a dashed line and a solid line in the Formula (I) represents, as described in the above, a double bond or a single bond; however, it is preferably a single bond.

Further, in the Formula (I), $R^1$ is preferably methyl, ethyl, propyl, butyl, isobutyl, cyclopropylmethyl, allyl, benzyl or phenethyl, more preferably cyclopropylmethyl or allyl.

It is preferred that $R^2$ and $R^3$ independently be hydrogen, hydroxy, acetoxy or methoxy.

It is preferred that A be —N($R^4$)C(=O)—, —N($R^4$)C(=O)O—, —N($R^4$)— or —N($R^4$)SO$_2$— (wherein $R^4$ represents hydrogen or $C_1$-$C_5$ linear or branched alkyl), and preferred thereamong is —N($R^4$)C(=O)— or —N($R^4$)C(=O)O— (wherein $R^4$ represents hydrogen or $C_1$-$C_5$ linear or branched alkyl).

It is preferred that B be $C_1$-$C_3$ linear alkylene, —CH=CH—, —C≡C—, —CH$_2$O— or —CH$_2$S—, and preferred thereamong is $C_1$-$C_3$ linear alkylene, —CH=CH— or —C≡C—.

It is preferred that $R^5$ be hydrogen or an organic group having a basic skeleton shown below (with the proviso that the organic group is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy).

[Formula 3]

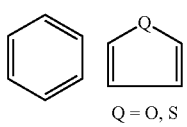

Q = O, S

Organic groups represented by $R^5$

It is preferred that $R^6$ be hydrogen.

Examples of pharmacologically preferred acid addition salt include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt, and preferred thereamong are hydrochloric acid salt, hydrobromic acid salt, phosphoric acid salt, tartaric acid salt, maleic acid salt, methanesulfonic acid salt and the like; however, of course, the pharmacologically preferred acid addition salt is not restricted thereto.

In the present invention, particularly preferred as the 4,5-epoxymorphinan derivative represented by the Formula (I) or a pharmacologically acceptable salt thereof are 17-(cyclopropylmethyl)-3,14β-dihydroxy-4,5α-epoxy-6β-[N-methyl-trans-3-(3-furyl)acrylamido]morphinan hydrochloric acid salt (hereinafter, referred to as Compound 1) and 17-(cyclopropylmethyl)-3,14β-dihydroxy-4,5α-epoxy-6β-[N-methyl-3-(4-trifluoromethylphenyl)propiolamido]morphinan hydrochloric acid salt (hereinafter, referred to as Compound 2).

[Formula 4]

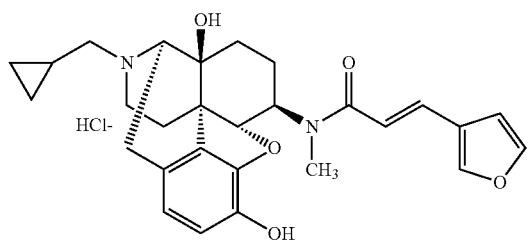

(Compound 1)

[Formula 5]

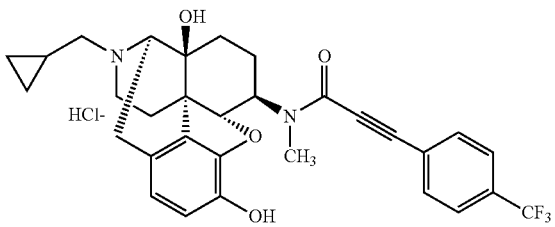

(Compound 2)

The 4,5-epoxymorphinan derivative or a pharmacologically acceptable acid addition salt thereof, which is the medicinal component in the tablet of the present invention, can be produced, for example, in accordance with the method described in Japanese Patent No. 2525552 or WO 93/15081.

The content of the 4,5-epoxymorphinan derivative or a pharmacologically acceptable acid addition salt thereof, which is the medicinal component in the tablet of the present invention, is not particularly restricted as long as it is a therapeutically effective amount. For example, it can be in the range of 0.01 to 10,000 μg/preparation, and it is usually in the range of 0.1 to 1,000 μg/preparation.

The indispensable component (2) of the tablet according to the present invention is sodium thiosulfate. As sodium thiosulfate used in the present invention, any of the generally commercially available ones may be employed. Sodium thiosulfate may be an anhydride or a hydrate (pentahydrate); however, it is preferably a hydrate. The content thereof may be any amount as long as it is not greater than 5% by weight per unit weight containing the effective ingredient; however, it is preferably not greater than 0.5% by weight. The lower limit of the content is not particularly restricted; however, it is usually not less than 0.00001% by weight per unit weight containing the effective ingredient.

The indispensable component (3) of the tablet according to the present invention is at least one selected from the group consisting of saccharides and sugar alcohols. As the saccharide and/or sugar alcohol used in the present invention, any of the generally commercially available ones may be employed. Examples of the saccharide and/or sugar alcohol include potato starch, saccharose, lactose, mannitol, erythritol and maltitol, and preferred thereamong is mannitol. In the present invention, as the indispensable component (3), the saccharide and sugar alcohol may be used individually or two or more thereof may be used in combination. The content thereof is not particularly restricted; however, with respect to the unit weight of the preparation containing the effective ingredient, it is usually not less than 75% by weight and may be any amount not less than 80% by weight, and it is preferably not less than 85% by weight, more preferably not less than 90% by weight. Further, the particle form of the saccharide and/or sugar alcohol used is not particularly restricted and it may be granulated granules, powder, fine powder; however, from the standpoint of the advantage in handling, it is preferred that the saccharide and/or sugar alcohol be in the form of granulated granules in its partial or the entire amount. In the present invention, the term, the saccharide and/or sugar alcohol which is/are the indispensable component (3) "is/are partially or entirely in the form of granulated granules", means either of the followings: to prepare the tablet of the present invention by mixing a part of or the entirety of the saccharide and/or sugar alcohol in the form of granulated granules with other raw material(s); and to, after mixing a part of or the entirety of the saccharide and/or sugar alcohol in the form of powder with (a partial or the entire amount of) other raw material(s), granulate the resulting mixture into granules to subsequently prepare therefrom the tablet of the present invention. In the former case, commercially available granulated granule may be used or granulated granule prepared from powder-form saccharide and/or sugar alcohol may also be used. Examples of powder mannitol include PEARLITOL (registered trademark) 50C manufactured by Roquette Japan K.K. Meanwhile, as the granulated granule, those produced by any of the known techniques such as spray drying, extrusion granulation, stirring granulation and fluidized bed granulation may also be used. Spray-dried granules or extrusion-granulated granules are preferably used since no tableting problem occurs and high tablet hardness can be attained. Examples of known mannitol granulated granules include spray-dried granule PEARLITOL (registered trademark) 200SD and extrusion-granulated granule PEARLITOL (registered trademark) 300DC, both of which are manufactured by Roquette Japan K.K. In addition, when the particle diameter of the saccharide or sugar alcohol is small, tableting problem easily occurs and when the particle diameter is large, high tablet hardness is not likely to be attained; therefore, for example, an average particle diameter may be, when measured in accordance with the particle size measurement method described in the Japanese Pharmacopeia 15th Edition, not less than 10 μm, and it is preferably not less than 30 μm, more preferably not less than 50 μm. Further, the upper limit of the particle diameter is usually not greater than 3,000 μm, particularly 1,000 μm; however, it is not restricted thereto.

The indispensable component (4) of the tablet according to the present invention is crospovidone, sodium carboxymethyl starch or a mixture thereof. As the crospovidone or sodium carboxymethyl starch used in the present invention, any of the generally commercially available ones may be employed. Examples of specific commercial products of crospovidone include Kollidon (registered trademark) CL, CL-M, CL-F and CL-SF which are manufactured by BASF, as well as Polyplasdone XL, XL-10 and INF-10 which are manufactured by IPS Ltd. Examples of specific commercial products of sodium carboxymethyl starch include Explotab (registered trademark) and VIVASTAR (registered trademark) manufactured by JRS, Primojel (registered trademark) manufactured by DMV, and Glycolys (registered trademark) manufactured by Roquette Japan K.K. The content of crospovidone or sodium carboxymethyl starch (the total amount when a mixture thereof is used) may be 1 to 20% by weight per unit weight containing the above-described effective ingredient. In order to ensure better quality and performance of the tablet, the content may be preferably in the range of 2 to 15% by weight, more preferably 5 to 10% by weight.

In the tablet according to the present invention, in addition to the indispensable components (1) to (4) described in the above, a pharmacologically acceptable additive such as lubricant, flavoring agent or coloring agent may also be added as required. Examples of the lubricant include magnesium stearate, calcium stearate, talc, stearic acid, sucrose fatty acid ester and light anhydrous silicic acid.

In the tablet according to the present invention, in addition to the indispensable components (1) to (4) described in the above, a pharmacologically acceptable vehicle, disintegrating agent or binding agent may also be added as required. For example, xylitol, sorbitol, low-substituted hydroxypropyl cellulose, crystalline cellulose, hydroxypropyl cellulose, partially-pregelatinized starch, croscarmellose sodium, carboxymethyl cellulose or the like may also be added as appropriate.

The tablet according to the present invention can be produced in accordance with a known method by using the above-described indispensable components and arbitrary components (which include those having a role as a vehicle). The term "tablet" used herein also encompasses, in addition to those conventional tablets taken with water, fast-disintegrating tablets such as one described in WO 2006-038661 which have extremely quick disintegration property and can be normally disintegrated intraorally within one minute only with an extremely small amount of water content such as saliva, as well as intraorally-disintegrating tablets such as one described in Patricia Van Arnum, "Advancing ODT Technology", Pharmaceutical Technology, Vol. 3, No. 10 pp. 66-76, 2007 (published on Oct. 2, 2007), which are normally disintegrated and dissolved intraorally without water within 60 seconds.

The tablet according to the present invention cay be produced by a wet granulation method comprising the steps of dissolving or suspending the above-described effective ingredient (1) in water or a pharmacologically acceptable solvent and adding the resulting liquid (solution or suspension) to the saccharide or sugar alcohol. The addition of sodium thiosulfate or that of crospovidone or sodium carboxymethyl starch can be carried out by an arbitrary step. For example, sodium thiosulfate may be dissolved or suspended together with the effective ingredient in water or a pharmacologically acceptable solvent and then added to the saccharide or sugar alcohol. Crospovidone and/or sodium carboxymethyl starch may also be dissolved or suspended together with the effective ingredient in water or pharmacologically acceptable solvent and then added to the saccharide or sugar alcohol. Alternatively, crospovidone and/or sodium carboxymethyl starch may be added after adding sodium thiosulfate and the effective ingredient to the saccharide or sugar alcohol and appropriately subjecting the resultant to granulation or size selection. Further, the entire amount of the saccharide or sugar alcohol may be added in the aforementioned step of adding the effective ingredient, or only a partial amount of the saccharide or sugar alcohol may be used in the step, adding the remaining amount in a later step.

In the wet granulation, a commonly used apparatus is employed, and examples thereof include fluidized bed granulators, tumbling fluidized bed granulators, stirring granulators, cylindrical extrusion granulators and wet extrusion granulators. In cases where water is used as the solvent for dissolving or suspending the effective ingredient, a fluidized bed granulator and a tumbling fluidized bed granulator capable of drying with spraying are suitable. Further, in cases where a volatile solvent such as ethanol is used as the solvent for dissolving or suspending the effective ingredient, a fluidized bed granulator, a tumbling fluidized bed granulator and a stirring granulator are suitable.

As the apparatus for mixing the preparation, a commonly used apparatus is employed, and examples thereof include V-shaped mixers, ribbon mixers and air blenders.

For compression molding, a commonly used apparatus is employed, and examples thereof include single-punch tableting machines and rotary tableting machines. The molding pressure in tableting is not particularly restricted and may be any pressure as long as the resulting tablet has such a tablet hardness that would not be an issue in handling. For example, the tableting pressure may be set at 200 to 10,000 $kgf/cm^2$, preferably 500 to 5,000 $kgf/cm^2$.

The amount of the lubricant to be added is not particularly restricted; however, for example, in the case of magnesium stearate, the amount is preferably about 0.1 to 5.0% by weight, more preferably 0.5 to 3.0% by weight per unit weight containing the effective ingredient.

The thus obtained tablet according to the present invention comprising a morphinan derivative represented by the Formula (I) or a pharmacologically acceptable acid addition salt thereof as the effective ingredient can be made into a coated preparation by adding a coating agent as required. As the coating agent, a functional base may be selected in accordance with the purpose and, for example, any of the generally commercially available ones, such as hydroxypropylmethyl cellulose, ethyl cellulose, carboxymethylethyl cellulose and premixed products thereof, may be used.

For film coating operation, a commonly used apparatus is employed, and a pan coating machine is suitable for producing film-coated tablets.

EXAMPLES

In order to clarify the superior effects of the present invention, the present invention will now be explained by way of examples thereof; however, the present invention is not restricted thereto. It is noted here that, in the following examples, PEARLITOL (registered trademark) 200SD which is a spray-dried granule of mannitol, PEARLITOL (registered trademark) 300DC which is a extrusion-granulated granule of mannitol and PEARLITOL (registered trademark) 50C which is a powder-form mannitol are abbreviated as "mannitol SD", "mannitol DC" and "mannitol C", respectively (all of these products are manufactured by Roquette Japan K.K.). Further, the "Compound 1" is, as stated in the above, 17-(cyclopropylmethyl)-3,14β-dihydroxy-4,5α-epoxy-6β-[N-methyl-trans-3-(3-furyl)acrylamido]morphinan hydrochloric acid salt Example 1

Mannitol SD was weighed in an amount of 126.645 parts by weight (hereinafter, abbreviated as "parts" and the same applies in the followings unless otherwise specified). It was then sieved through a mesh having 1 mm openings and placed into a mortar. The thus obtained granules were mixed for 5 minutes in the mortar while spraying thereto a spray solution in which 0.005 parts of the Compound 1 and 0.1 parts of sodium thiosulfate hydrate (Kokusan Chemical Co., Ltd.) were dissolved in distilled water. The resultant was dried at 45° C. for 2 hours using a hot-air dryer (PS-212, Espec Corporation) to produce granulated granules. The granulated granules were subjected to size selection using a comil (197S, Powrex Corporation) and added with 2.6 parts of crospovidone (Kollidon (registered trademark) CL, BASF), and the resultant was mixed for 15 minutes using a V-shaped mixer (Tsutsui Scientific Instruments Co., Ltd.). To the thus obtained mixture, 0.65 parts of magnesium stearate (Taihei Chemical Industrial Co., Ltd.) was further added, and the resultant was mixed for 5 minutes. The thus obtained granules were made into a tablet of 130 mg using a tableting machine (Correct 19, Kikusui Seisakusho Ltd.).

Example 2

Mannitol SD was weighed in an amount of 38.475 parts, sieved through a mesh having 1 mm openings and loaded into a fluidized bed granulator (FLO-5, Freund Corporation). A spray solution in which 0.005 parts of the Compound 1 and 0.1 parts of sodium thiosulfate hydrate were dissolved in distilled water was sprayed to the thus obtained granules to produce granulated granules. The granulated granules were processed using the comil to obtain size-selected granules. To 38.58 parts of the thus obtained size-selected granules, 84.27 parts of mannitol SD and 6.5 parts of crospovidone were added, and the resultant was mixed for 15 minutes using the V-shaped mixer. To the thus obtained mixture, 0.65 parts of magnesium stearate (Taihei Chemical Industrial Co., Ltd.) was further added, and the resultant was mixed for 5 minutes. The thus obtained granules were made into a tablet of 130 mg using a tableting machine (Correct 19, Kikusui Seisakusho Ltd.).

Example 3

A tablet was produced in the same manner as in Example 2, except that mannitol SD and crospovidone were added in an amount of 77.77 parts and 13 parts, respectively, to 38.58 parts of the size-selected granules of Example 2.

Example 4

A tablet was produced in the same manner as in Example 2, except that mannitol SD and crospovidone were added in an amount of 71.27 parts and 19.5 parts, respectively, to 38.58 parts of the size-selected granules of Example 2.

Example 5

A tablet was produced in the same manner as in Example 1, except that the content of mannitol SD of Example 1 was 103.245 parts and that of crospovidone was 26 parts.

Example 6

Mannitol SD was weighed in an amount of 96.745 parts, sieved through a mesh having 1 mm openings and loaded into a fluidized bed granulator (FLO-5, Freund Corporation). A spray solution in which 0.005 parts of the Compound 1 and 0.1 parts of sodium thiosulfate hydrate were dissolved in distilled water was sprayed to the thus obtained granules to produce granulated granules. Next, mannitol C was weighed in an amount of 26 parts, sieved through a mesh having 1 mm openings and, along with 6.5 parts of crospovidone, loaded into a stirring granulator (NMG-3L, Nara Machinery Co., Ltd.). Subsequently, the thus loaded mixture was granulated while adding thereto distilled water to produce granules. The granulated granules produced by the fluidized bed granulator and those produced by the stirring granulator were respectively processed using the comil to obtain size-selected granules. To 129.35 parts of the thus size-selected granules, 0.65 parts of magnesium stearate (Taihei Chemical Industrial Co., Ltd.) was added, and the resultant was mixed for 5 minutes. The thus obtained granules were made into a tablet of 130 mg using a tableting machine (Correct 19, Kikusui Seisakusho Ltd.).

Example 7

A tablet was produced in the same manner as in Example 1, except that mannitol SD of Example 1 was replaced with different grade mannitols, mannitol DC and mannitol C, in an amount of 96.745 parts and 26 parts, respectively, and that the content of crospovidone was 6.5 parts.

Example 8

A tablet was produced in the same manner as in Example 1, except that mannitol SD of Example 1 was replaced with lactose (Pharmatose (registered trademark) 200M, DMV) in an amount of 122.095 parts and that the contents of crospovidone and magnesium stearate were 6.5 parts and 1.3 parts, respectively.

Example 9

A tablet was produced in the same manner as in Example 1, except that mannitol SD of Example 1 was partially replaced with erythritol (Nikken Chemical Laboratory Co., Ltd.) in such a manner that the contents of mannitol SD and erythritol were 83.095 parts and 39 parts, respectively, and that the contents of crospovidone and magnesium stearate were 6.5 parts and 1.3 parts, respectively.

Example 10

A tablet was produced in the same manner as in Example 1, except that mannitol SD of Example 1 was partially replaced with potato starch (ST-P, Nippon Starch Chemical Co., Ltd.) in such a manner that the contents of mannitol SD and potato starch were 83.095 parts and 39 parts, respectively, and that the contents of crospovidone and magnesium stearate were 6.5 parts and 1.3 parts, respectively.

Example 11

A tablet was produced in the same manner as in Example 1, except that mannitol SD of Example 1 was replaced with maltitol (powder maltitol G-3, Towa-Kasei Co., Ltd.) in an amount of 122.095 parts and that the contents of crospovidone and magnesium stearate were 6.5 parts and 1.3 parts, respectively.

Example 12

A tablet was produced in the same manner as in Example 1, except that mannitol SD of Example 1 was replaced with saccharose (Suzu Funmatsu Yakuhin K.K.) in an amount of 122.095 parts and that the contents of crospovidone and magnesium stearate were 6.5 parts and 1.3 parts, respectively.

Example 13

A tablet was produced in the same manner as in Example 2, except that mannitol SD and sodium carboxymethyl starch (EXPLOTAB (registered trademark), JRS Pharma) were added in an amount of 88.17 parts and 2.6 parts, respectively, to 38.58 parts of the size-selected granules of Example 2.

Example 14

A tablet was produced in the same manner as in Example 1, except that the content of mannitol SD of Example 1 was 116.245 parts and that crospovidone was replaced with sodium carboxymethyl starch in an amount of 13 parts.

Example 15

A tablet was produced in the same manner as in Example 1, except that the content of mannitol SD of Example 1 was 116.245 parts and that crospovidone was partially replaced with sodium carboxymethyl starch in such a manner that the contents of crospovidone and sodium carboxymethyl starch were both 6.5 parts each.

Comparative Example 1

Weighed in a standard bottle were 10 parts by weight of the Compound 1 and 100 parts of crystalline cellulose (Avicel (registered trademark) PH-101, Asahi Kasei Corporation). Distilled water in an amount of 30 parts was added thereto and the resultant was mixed with a glass rod. After drying the thus obtained granules, the dried granules were made into a tablet of 100 mg using a single-punch tableting machine (RIKEN POWER, Riken Seiki Co., Ltd.).

Comparative Example 2

A tablet was produced in the same manner as in Comparative Example 1, except that crystalline cellulose of Comparative Example 1 was replaced with polyvinyl alcohol (PVA EG-5, Nippon Synthetic Chemical Industry Co., Ltd.).

Comparative Example 3

A tablet was produced in the same manner as in Comparative Example 1, except that crystalline cellulose of Comparative Example 1 was replaced with hydroxypropyl cellulose (HPC-L (registered trademark), Nippon Soda Co., Ltd.).

Comparative Example 4

A tablet was produced in the same manner as in Comparative Example 1, except that crystalline cellulose of Comparative Example 1 was replaced with croscarmellose sodium (Ac-di-sol (registered trademark), FMC Bio Polymer) (hereinafter, abbreviated as Ac-di-sol).

Comparative Example 5

A tablet was produced in the same manner as in Comparative Example 1, except that crystalline cellulose of Comparative Example 1 was replaced with carmellose calcium (CMC-Ca ECG-505, Gotoku Chemical Co., Ltd.) (hereinafter, abbreviated as CMC-Ca).

Comparative Example 6

A solid preparation was produced in accordance with the technique described in WO 99/02158 (Patent Document 2). Lactose and crystalline cellulose were weighed in an amount of 49.91 parts and 26.4 parts, respectively, and loaded into the fluidized bed granulator. A spray solution in which 0.01 parts of the Compound 1, 0.08 parts of sodium thiosulfate hydrate and 3.2 parts of hydroxypropyl cellulose (HPC-SL (registered trademark), Nippon Soda Co., Ltd.) were dissolved in distilled water was sprayed to the thus obtained formulation powder to produce granulated granules. The granulated granules were processed using the comil to obtain size-selected granules. To 79.6 parts of the thus obtained size-selected granules, 0.4 parts of magnesium stearate was added, and the resultant was mixed for 5 minutes. The thus obtained granules were made into a tablet of 80 mg using the tableting machine.

Comparative Example 7

Mannitol SD was weighed in an amount of 78.895 parts, sieved through a mesh having 1 mm openings and loaded into a fluidized bed granulator (FLO-5, Freund Corporation). A spray solution in which 0.005 parts of the Compound 1 and 0.1 parts of sodium thiosulfate hydrate were dissolved in distilled water was sprayed to the thus obtained granules to produce drug-carrying granules. To 79 parts of the thus obtained drug-carrying granules, 15 parts of mannitol SD and 5 parts of Ac-di-sol were added, and the resultant was mixed for 15 minutes using a V-shaped mixer (permeation-mode S-5, Tsutsui Scientific Instruments Co., Ltd.). To the thus obtained mixture, 1 part of magnesium stearate was further added, and the resultant was mixed for 5 minutes. The thus obtained granules were made into a tablet of 100 mg using the tableting machine.

Comparative Example 8

Drug-carrying granules were prepared in the same manner as in Comparative Example 7, and the subsequent mixing and tableting were carried out in the same manner as in Comparative Example 7, except that 10 parts of mannitol SD and 10 parts of CMC-Ca in place of Ac-di-sol were added to 79 parts of the drug-carrying granules.

Comparative Example 9

A tablet was produced in the same manner as in Example 1, except that the content of mannitol SD was 90.245 parts and that of crospovidone was 39 parts.

Comparative Example 10

A tablet was produced in the same manner as in Example 1, except that the content of mannitol SD was 77.245 parts and that of crospovidone was 52 parts.

Comparative Example 11

A tablet was produced in the same manner as in Example 2, except that the content of mannitol SD was 122.845 parts and that sodium thiosulfate hydrate was not added.

Example 16

The tablets obtained in each of Examples 1 to 15 and Comparative Examples 1 to 11 were left to stand in an open state under the condition of 40° C./75% RH, which is the acceleration condition described in the Drug Approval and Licensing Procedures in Japan (2006), and the residual ratio (%) of the drug was subsequently measured by HPLC method to evaluate the stability thereof (Tables 1 and 2).

As shown in Tables 1 and 2, for Comparative Example 6 in which saccharide and sodium thiosulfate were blended without crospovidone and for Comparative Example 11 in which sugar alcohol and crospovidone were blended without sodium thiosulfate, the drug residual ratio was measured to be low at 94.4% and 83.3%, respectively. In addition, Comparative Examples 1 to 5, 7 and 8 in which crospovidone or sodium carboxymethyl starch was not blended and Comparative Examples 9 and 10 in which the content of crospovidone was not less than 30% also exhibited low residual ratios. In contrast, those tablets described in Examples 1 to 15, which comprise sodium thiosulfate, saccharide or sugar alcohol, and 1 to 20% by weight of crospovidone, sodium carboxymethyl starch or a mixture thereof per unit weight containing the effective ingredient, all exhibited a residual ratio of not less than 96% even when they were stored unpacked for one month under the condition of 40° C. and 75% RH, and showed a prominent stabilization effect as compared to the formulations of Comparative Examples; therefore, it was demonstrated that those tablets of Examples 1 to 15 can ensure sufficient stability also when handled as a pharmaceutical.

TABLE 1

| Formulated Component | Example 1 | Example 2 | Example 3 | Example 4 | Example 5 | Example 6 | Example 7 | Example 8 |
|---|---|---|---|---|---|---|---|---|
| Compound 1 | 0.0038 | 0.0038 | 0.0038 | 0.0038 | 0.0038 | 0.0038 | 0.0038 | 0.0038 |
| Mannitol SD | 97.419 | 94.419 | 89.419 | 84.419 | 79.419 | 74.419 | — | — |
| Mannitol DC | — | — | — | — | — | — | 74.4192 | — |
| Mannitol C | — | — | — | — | — | 20 | 20 | — |
| Lactose | — | — | — | — | — | — | — | 93.919 |
| Erythritol | — | — | — | — | — | — | — | — |
| Potato starch | — | — | — | — | — | — | — | — |
| Maltitol | — | — | — | — | — | — | — | — |
| Refined sucrose | — | — | — | — | — | — | — | — |
| Crospovidone | 2 | 5 | 10 | 15 | 20 | 5 | 5 | 5 |
| Sodium carboxymethyl starch | — | — | — | — | — | — | — | — |
| Sodium thiosulfate hydrate | 0.077 | 0.077 | 0.077 | 0.077 | 0.077 | 0.077 | 0.077 | 0.077 |
| Magnesium stearate | 0.5 | 0.5 | 0.5 | 0.5 | 0.5 | 0.5 | 0.5 | 1 |
| Total | 100 | 100 | 100 | 100 | 100 | 100 | 100 | 100 |

TABLE 1-continued

| | | | | | | | | |
|---|---|---|---|---|---|---|---|---|
| Residual ratio (%) after the tablet was left to stand for one month in an open state under the condition of 40° C. and 75% RH | 99.1 | 98.9 | 97.9 | 98.2 | 98.2 | 99.1 | 99.6 | 96.1 |

| Formulated Component | Example 9 | Example 10 | Example 11 | Example 12 | Example 13 | Example 14 | Example 15 |
|---|---|---|---|---|---|---|---|
| Compound 1 | 0.0038 | 0.0038 | 0.0038 | 0.0038 | 0.0038 | 0.0038 | 0.0038 |
| Mannitol SD | 63.919 | 63.919 | — | — | 97.419 | 89.419 | 89.419 |
| Mannitol DC | — | — | — | — | — | — | — |
| Mannitol C | — | — | — | — | — | — | — |
| Lactose | — | — | — | — | — | — | — |
| Erythritol | 30 | — | — | — | — | — | — |
| Potato starch | — | 30 | — | — | — | — | — |
| Maltitol | — | — | 93.919 | — | — | — | — |
| Refined sucrose | — | — | — | 93.919 | — | — | — |
| Crospovidone | 5 | 5 | 5 | 5 | — | — | 5 |
| Sodium carboxymethyl starch | — | — | — | — | 2 | 10 | 5 |
| Sodium thiosulfate hydrate | 0.077 | 0.077 | 0.077 | 0.077 | 0.077 | 0.077 | 0.077 |
| Magnesium stearate | 1 | 1 | 1 | 1 | 0.5 | 0.5 | 0.5 |
| Total | 100 | 100 | 100 | 100 | 100 | 100 | 100 |
| Residual ratio (%) after the tablet was left to stand for one month in an open state under the condition of 40° C. and 75% RH | 97.2 | 97.9 | 99.2 | 97.4 | 101.7 | 96.9 | 98.8 |

Blend unit of the formulated components: indicated in % by weight based on unit weight of the preparation

TABLE 2

| Formulated Component | Comparative Example 1 | Comparative Example 2 | Comparative Example 3 | Comparative Example 4 | Comparative Example 5 | Comparative Example 6 |
|---|---|---|---|---|---|---|
| Compound 1 | 9.1 | 9.1 | 9.1 | 9.1 | 9.1 | 0.0125 |
| Mannitol SD | — | — | — | — | — | — |
| Lactose | — | — | — | — | — | 62.3875 |
| Crystalline cellulose | 90.9 | — | — | — | — | 33 |
| Crospovidone | — | — | — | — | — | — |
| Polyvinyl alcohol | — | 90.9 | — | — | — | — |
| Hydroxypropyl cellulose | — | — | 90.9 | — | — | 4 |
| Ac-di-sol | — | — | — | 90.9 | — | — |
| CMC-Ca | — | — | — | — | 90.9 | — |
| Sodium thiosulfate hydrate | — | — | — | — | — | 0.1 |
| Magnesium stearate | — | — | — | — | — | 0.5 |
| Total | 100 | 100 | 100 | 100 | 100 | 100 |
| Residual ratio (%) after the tablet was left to stand for 2 weeks in an open state under the condition of 40° C. and 75% RH | 93.0 | 87.1 | 92.2 | 93.7 | 90.2 | — |
| Residual ratio (%) after the tablet was left to stand for one month in an open state under the condition of 40° C. and 75% RH | — | — | — | — | — | 94.4 |

| Formulated Component | Comparative Example 7 | Comparative Example 8 | Comparative Example 9 | Comparative Example 10 | Comparative Example 11 |
|---|---|---|---|---|---|
| Compound 1 | 0.005 | 0.005 | 0.0038 | 0.0038 | 0.0038 |
| Mannitol SD | 93.895 | 88.895 | 69.419 | 59.419 | 94.496 |
| Lactose | — | — | — | — | — |
| Crystalline cellulose | — | — | — | — | — |
| Crospovidone | — | — | 30 | 40 | 5 |
| Polyvinyl alcohol | — | — | — | — | — |
| Hydroxypropyl cellulose | — | — | — | — | — |
| Ac-di-sol | 5 | — | — | — | — |
| CMC-Ca | — | 10 | — | — | — |

TABLE 2-continued

| | | | | | |
|---|---|---|---|---|---|
| Sodium thiosulfate hydrate | 0.1 | 0.1 | 0.077 | 0.077 | — |
| Magnesium stearate | 1 | 1 | 0.5 | 0.5 | 0.5 |
| Total | 100 | 100 | 100 | 100 | 100 |
| Residual ratio (%) after the tablet was left to stand for 2 weeks in an open state under the condition of 40° C. and 75% RH | — | — | — | — | — |
| Residual ratio (%) after the tablet was left to stand for one month in an open state under the condition of 40° C. and 75% RH | 93.7 | 93.0 | 86.0 | 79.1 | 83.3 |

Blend unit of the formulated components: indicated in % by weight based on unit weight of the preparation

Example 17

Mannitol SD was weighed in an amount of 38.475 parts, sieved through a mesh having 1 mm openings and loaded into the fluidized bed granulator. Then, a spray solution in which 0.005 parts of the Compound 1 and 0.1 parts of sodium thiosulfate hydrate were dissolved in distilled water was sprayed to the thus obtained granules to produce granulated granules. The granulated granules were processed using the comil to obtain size-selected granules. To 38.58 parts of the thus obtained size-selected granules, 84.27 parts of mannitol SD and 6.5 parts of crospovidone were added, and the resultant was mixed for 15 minutes using the V-shaped mixer. To the thus obtained mixture, 0.65 parts of magnesium stearate (Taihei Chemical Industrial Co., Ltd.) was further added, and the resultant was mixed for 5 minutes. The thus obtained granules were made into a tablet of 130 mg using a tableting machine (Correct 19, Kikusui Seisakusho Ltd.). Next, this tablet was loaded into a film coating machine (Hicoater Mini, Freund Corporation) and a solution in which OPADRY-OY7300 (Japan Colorcon) was dissolved or dispersed was sprayed to the tablet to produce a coated tablet of 137 mg in which 7 mg of coating agent was added to 130 mg of the tablet.

Example 18

Mannitol DC was weighed in an amount of 96.745 parts, sieved through a mesh having 1 mm openings and loaded into the fluidized bed granulator. Then, a spray solution in which 0.005 parts of the Compound 1 and 0.1 parts of sodium thiosulfate hydrate were dissolved in distilled water was sprayed to the thus obtained granules to produce granulated granules. Then, mannitol C was weighed in an amount of 25.9675 parts, sieved through a mesh having 1 mm openings and, along with 6.5 parts of crospovidone, loaded into the stirring granulator. Subsequently, the thus loaded mixture was granulated while adding thereto distilled water into which 0.0325 parts of iron sesquioxide was dispersed, thereby producing granulated granules. The granulated granules produced by the fluidized bed granulator and those produced by the stirring granulator were respectively processed using the comil to obtain size-selected granules. To 129.35 parts of the thus size-selected granules, 0.65 parts of magnesium stearate was added, and the resultant was mixed for 5 minutes. The thus obtained granules were made into a WR tablet of 130 mg using the tableting machine.

Example 19

For the tablet obtained in Example 18, the intraoral disintegration time in three subjects consisting of a healthy adult male and female was measured. The time required for the tablet to be completely disintegrated by saliva without taking water into the mouth and chewing the tablet (the time required for the subject to no longer have a feel of foreign matter in the mouth) was measured, and the average of the measurements for the three subjects was used as the intraoral disintegration time. As the result, the intraoral disintegration time was approximately 9 seconds; therefore, it was confirmed that the tablet has excellent disintegration property.

The invention claimed is:

1. A tablet comprising the following (1) to (4):
(1) as an effective ingredient, a 4,5-epoxymorphinan derivative represented by the Formula (I);

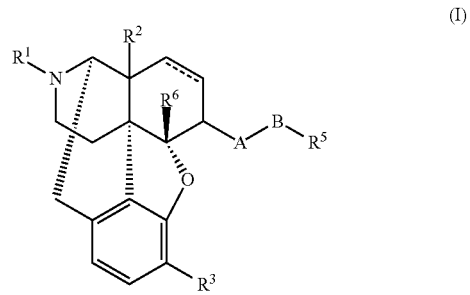

wherein,
the double line composed of a dashed line and a solid line represents a double bond or a single bond;
$R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, $C_1$-$C_5$ furan-2-ylalkyl or $C_1$-$C_5$ thiophen-2-ylalkyl;
$R^2$ represents hydrogen, hydroxy, nitro, $C_1$-$C_5$ alkanoyloxy, $C_1$-$C_5$ alkoxy, $C_1$-$C_5$ alkyl or —$NR^7R^8$;
$R^7$ represents hydrogen or $C_1$-$C_5$ alkyl;

$R^8$ represents hydrogen, $C_1$-$C_5$ alkyl or —C(=O)$R^9$;

$R^9$ represents hydrogen, phenyl or $C_1$-$C_5$ alkyl;

$R^3$ represents hydrogen, hydroxy, $C_1$-$C_5$ alkanoyloxy or $C_1$-$C_5$ alkoxy;

A represents —N($R^4$)C(=X)—, —N($R^4$)C(=X)Y—, —N($R^4$)— or —N($R^4$)SO$_2$— (wherein X and Y independently represent N$R^4$, S or O; $R^4$ represents hydrogen, $C_1$-$C_5$ linear or branched alkyl or $C_6$-$C_{12}$ aryl; and $R^4$ in the formula may be the same or different);

B represents a valence bond, $C_1$-$C_{14}$ linear or branched alkylene (with the provisos that said alkylene is optionally substituted by at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl, trifluoromethoxy and phenoxy, and that 1 to 3 methylene groups may be substituted by carbonyl group(s)), $C_2$-$C_{14}$ linear or branched acyclic unsaturated hydrocarbon containing 1 to 3 double bonds and/or triple bonds (with the provisos that said acyclic unsaturated hydrocarbon is optionally substituted by at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl, trifluoromethoxy and phenoxy, and that 1 to 3 methylene groups may be substituted by carbonyl group(s)) or $C_1$-$C_{14}$ linear or branched saturated or unsaturated hydrocarbon containing 1 to 5 thioether bonds, ether bonds and/or amino bonds (with the provisos that a hetero atom does not directly binds to A, and that 1 to 3 methylene groups may be substituted by carbonyl group(s));

$R^5$ represents hydrogen or organic group having a basic skeleton shown below (with the proviso that said organic group is optionally substituted by at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy);

Q: N, O, S
T: CH, N, S, O
l = 0-5
m, n ≥ 0
m + n ≤ 5

Organic groups represented by $R^5$ and $R^6$ represents hydrogen, $C_1$-$C_5$ alkyl or $C_1$-$C_5$ alkanoyl, or a pharmacologically acceptable acid addition salt thereof;

(2) sodium thiosulfate;

(3) at least one selected from the group consisting of saccharides and sugar alcohols; and (4) crospovidone, sodium carboxymethyl starch or a mixture thereof, wherein the content of said (2) is not greater than 5%, said (3) is not less than 75% and said (4) is 1 to 20%, by weight per unit weight containing said effective ingredient.

2. The tablet according to claim 1, wherein said (3) is at least one selected from the group consisting of potato starch, saccharose, lactose, mannitol, erythritol and maltitol.

3. The tablet according to claim 1, wherein a part or the entirety of said (3) is granulated granules.

4. The tablet according to claim 3, wherein said granulated granules are produced by extrusion granulation, stirring granulation, spray drying or fluidized bed granulation.

5. The tablet according, to claim 1, said tablet being produced by a production method comprising the steps of dissolving or suspending said effective ingredient in water or a pharmacologically acceptable solvent and adding the resulting liquid to said sacchaide or sugar alcohol.

6. The tablet according to claim 1, wherein said tablet is in a coated form.

7. The tablet according to claim 1, wherein the sodium thiosulfate is present in an amount of not less than 0.00001% by weight.

8. The tablet according to claim 7, wherein the sodium thiosulfate is present in an amount of not more than 0.5% by weight.

9. The tablet according to claim 1, wherein component (4) is crospovidone.

10. The tablet according to claim 1, wherein component (4) is sodium carboxymethyl starch.

11. The tablet according to claim 8, wherein component (4) is crospovidone.

12. The tablet according to claim 8, wherein component (4) is sodium carboxymethyl starch.

* * * * *